United States Patent [19]

Kunihiro et al.

[11] Patent Number: 5,300,490

[45] Date of Patent: * Apr. 5, 1994

[54] ANTICOAGULANT SUBSTANCE OBTAINED FROM URINE

[75] Inventors: Yasuyuki Kunihiro; Ryo Tanaka; Michio Ichimura, all of Fujieda; Akio Uemura, Numazu; Nobuo Ohzawa, Shizuoka; Ei Mochida, Tokyo, all of Japan

[73] Assignee: Mochida Pharmaceutical Co., Ltd., Tokyo, Japan

[*] Notice: The portion of the term of this patent subsequent to Apr. 13, 2010 has been disclaimed.

[21] Appl. No.: 932,559

[22] Filed: Aug. 20, 1992

Related U.S. Application Data

[62] Division of Ser. No. 456,178, Dec. 26, 1989, Pat. No. 5,202,421.

[30] Foreign Application Priority Data

Dec. 27, 1988 [JP] Japan ................... 63-330413
Nov. 1, 1989 [JP] Japan ................... 1-285240

[51] Int. Cl.$^5$ ............................................ C07K 15/14
[52] U.S. Cl. ................................... 514/8; 530/395; 530/397; 514/12; 514/21
[58] Field of Search .................. 530/350, 397, 395; 514/8, 12, 21

[56] References Cited

U.S. PATENT DOCUMENTS

| | | |
|---|---|---|
| 3,723,251 | 3/1973 | Ogawa et al. |
| 4,638,050 | 1/1987 | Aoki et al. ............... 530/399 X |
| 4,732,891 | 3/1988 | Maki et al. ............... 514/21 |
| 4,748,156 | 5/1988 | Aoki et al. ............... 514/21 |
| 4,845,078 | 7/1989 | Masaoka ............... 514/8 |
| 4,873,222 | 10/1989 | Arai et al. ............... 514/21 |
| 5,043,425 | 8/1991 | Aoki et al. ............... 514/21 X |
| 5,047,503 | 9/1991 | Aoki et al. ............... 514/8 |
| 5,202,421 | 4/1993 | Kunihiro et al. ............... 530/350 |

FOREIGN PATENT DOCUMENTS

| | | |
|---|---|---|
| 0290419 | 11/1986 | European Pat. Off. |
| 00230945 | 8/1987 | European Pat. Off. |
| 0312598 | 8/1987 | European Pat. Off. |
| 0253331 | 1/1988 | European Pat. Off. |
| 63-30423 | 2/1988 | Japan |
| 2-19399 | 1/1990 | Japan |
| 551949 | 7/1974 | Switzerland |

OTHER PUBLICATIONS

Wen et al.; Human Thrombomodulin: Complete cDNA sequence and chromosome localization of the gene, Biochem., vol. 26, pp. 4350–4357 (1987).

Suzuki et al.; Structure and expression of human thrombomodulin, a thrombin receptor on endothelium acting as a cofactor for protein C activation, Embo Journal, vol. 6 (7), pp. 1891–1897 (1987).

Jackman et al.; Human thrombomodulin gene is intron depleted: Nucleic acid sequences of the cDNA and gene predict protein structure and suggest sites of regulatory control, Proc. Nat. Acad. Sci. USA, vol. 84, pp. 6425–6429 (1987).

J. Biochem. 103, 281–285 (1988), Shirai et al.

Thrombosis Research, 37, 353–364 (1985) Aoki et al.

Yoshikawa et al.; "Protection of Endotoxin-Induced Disseminated Intravascular Coagulation in Rats by Gabexate Mesilate"; Kyoto Profectural Univ. of Med.; pp. 633–640.

Ishii et al.; Yakugakkai Abstract 6F05, 11-1, 1988.

Ishii et al.; "Thrombomodulin is Present in Human Plasma and Urine"; J. Clin. Invest., vol. 76, Dec. 1985, pp. 2178–2181.

Palareti et al.; Thrombosis and Haemostasis; "Effects of Gabexate Mesilate, a New Synthetic Serine Protease Inhibitor on Blood Coagulation in Patients with Dic"; Jour. International Soc. on Thrombosis and Haemostasis; No. 1, vol. 58, 1987, p. 420.

(List continued on next page.)

Primary Examiner—Howard E. Schain
Attorney, Agent, or Firm—Oliff & Berridge

[57] ABSTRACT

This invention relates to a novel anticoagulant substance in human urine, a process for its preparation and a pharmaceutical composition comprising the said substance for the prevention and/or treatment of diseases related to the disorders in blood coagulation system.

3 Claims, 3 Drawing Sheets

OTHER PUBLICATIONS

Schoendorf et al.; "Endotoxin-Induced Disseminated Intravascular Coagulation in Nonpregnant Rats"; Dept. of OB/GYN; NY School of Med; 1971; pp. 51–58.

Ng et al.; "Pasteurization of Antihemophilic Factor and Model Virus Inactivation Studies"; Thrombosis Research 39; 1985; pp. 439–447.

Zushi et al.; "The Last Three Consecutive Epidermal Growth Factor-Like Structures of Human Thrombomodulin Comprise the Minimum Functional Domain for Protein C-Activating Cofactor Activity and Anticoagulant Activity"; Jour. of Bio. Chem., vol. 264, No. 18, 1989, pp. 10351–10353.

Gomi et al.; "Minimum Functional Domain of Human Thrombomodulin for Protein C Activating Cofactor Activity and Anticoagulant Activity"; Jour. of the International Soc. on Thrombosis and Haemostasis; Thrombosis; Thrombosis and Haemostasis; Abstract 1039; 1989; p. 334.

Maruyama et al.; "Human Thrombomodulin is not an Efficient Inhibitor of the Procoagulant Activity of Thrombin"; J. Clin. Invest.; vol. 75, 1985; pp. 987–991.

Salem et al.; "Isolation and Characterization of Thrombomodulin from Human Placenta"; Jour. Bio. Chem., 1984; vol. 259, No. 19, 1984; pp. 12246–12251.

Suzuki et al.; "Functionally Active Thrombomodulin is Present in Human Platelets"; J. Biochem, 104, 1988, pp. 628–632.

Robbins et al.; "Plasmin and Plasminogen Activators: Kinetics, and Kinetics of Plasminogen Activation"; Annals N.Y. Acad. of Sci., 1981; pp. 588–591.

Kurosawa et al.; "A 10-KDA Cyanogen Bromide Fragment from the Epidermal Growth Factor Homology Domain of Rabbit Thrombomodulin Contains the Primary Thrombin Binding Site"; Jour. Bio. Chem; vol. 263, No. 13, 1988; pp. 5993–5996.

Shirai et al.; "Gene Structure of Human Thrombomodulin, a Cofactor for Thrombin-Catalyzed Activation of Protein C"; J. Biochem., 103, 281, 1988.

Sottrup-Jenson, L. et al.; "The Primary Structure of Human Plasminogen . . ."; Progress in Chemical Fibrinolysis and Thrombolysis, 3, 191, 1978.

Moroz, L. A., "Mini-Plasminogen: A Mechanism for Leukocyte Modulation of Plasminogen Activation by Urokinase", Blood, 58, 97; 1978.

White, W. F. et al.; "The Isolation and Characterization of Plasminogen Activators from Human Urine"; Biochemistry, 5, 2160, 1966.

Bernik, M. B. et al., "Production by Human Tissues in Culture of Immunologically Distinct, Multiple Molecular Weight Forms of Plasminogen Activators"; Annals New York Acad. of Sci.; 593–608, 1981.

Blauhut et al., "Substitution of Antithrombin III in Shock and Dic-A Randomized Study"; Thrombosis Research, vol. 39, No. 1, pp. 81–89, 1985.

Moake, J. L., "Disseminated Intravascular Coagulation"; Current Therapy, pp. 338–339, 1989.

Loscalzo; "Thrombolysis in the Management of Acute Myocardial Infarction and Unstable Angina Pectoris"; Drugs, pp. 192–204; 1985.

Ohno et al., "Fibrinolytic System in Comparison with Heparin or Aprotinin"; Thrombosis Research, vol. 24, No. 5/6, pp. 445–452, 1982.

Triantaphyllopoulos; "Effects of Human Antithrombin III on Mortality and Blood Coagulation Induced in Rabbits by Endotoxin"; Thromb Haemostas, vol. 51, No. 2; pp. 232–235; 1984.

Iosbe, "Inhibitory Effects of Gabexate Mesilate (Foy) on Experimental Dic"; Advanced Exp. Med. Biol., pp. 385–394, 1979.

Emerson, Jr. et al.; "Protection Against Disseminated Intravascular Coagulation and Death by Antithrombin-III in the Escherichia Coli Endotoxemic Rat"; Circulatory Shock; vol. 21; pp. 1–13, 1987.

Diffang et al.; "Effect of Trasylol on Fibrin Deposition and Elimination in the Lungs of Rats with Intravascular Coagulation Induced by Thrombin or Thromboplastin"; Thrombosis Research, vol. 5, pp. 263–276, 1974.

Suzuki, K. et al.; J. Bio. Chem., 264, 4872, 1989.

Rees, M. W., et al.; Chemical Abstracts, 85, 490, Abstract No. 6027r, 1976.

4 : HUMAN PLACENTAL THROMBOMODULIN
5 : TM1
6 : TM2

ANTICOAGULANT SUBSTANCE OBTAINED FROM URINE

This is a Division of U.S. patent application Ser. No. 07/456,178 filed Dec. 26, 1989 now U.S. Pat. No. 5,202,421

BACKGROUND OF THE INVENTION

The invention relates to a novel anticoagulant substance obtained from human urine, a process for its preparation and a pharmaceutical composition comprising the said substance for prevention and/or treatment of diseases related to the disorders in blood coagulation system.

As anticoagulant agents, heparin and antithrombin III are presently in use. Thrombolytic agents in use include urokinase, which is obtained from human urine or from cultured kidney cells, and streptokinase, which is extracted from beta-hemolytic streptococci. In addition, tissue plasminogen activator is now being developed.

On the other hand, it is well known that these drugs have side effects such as tendency of bleeding, and their anticoagulant or thrombolytic effect are not sufficient for the clinical use. In the field of fundamental investigation, an unknown substance was recently purified from rabbit lung extract and was identified as a novel physiological anticoagulant. The substance was named thrombomodulin [N. L. Esmon et al., J. Biol. Chem., Vol. 257, p.859 (1982)]. Thrombomodulin has two modes of action; an anticoagulant activity based on its anti-thrombin effect, and a fibrinolytic effect based on its stimulatory effect on thrombin-catalyzed protein C activation. Thrombomodulin is a receptor of thrombin on the endothelial cell surface, and, by binding thrombin, directly inhibits its procoagulant activity. Moreover, thrombin-thrombomodulin complex activates protein C which possesses a potent anticoagulant effect and a thrombolytic effect [I. Maruyama et al., J. Clin. Invest., Vol. 75, p.987 (1985)]. Since thrombomodulin exhibits not only an anticoagulant activity but also an enhancing effect on thrombolytic system, it is expected to be very useful for the treatment of blood coagulation disorders.

Since the thrombomodulin molecule mainly consists of peptides, thrombomodulin derived from the human, which has little antigenicity, ought to be administered to patients in order to avoid side effects such as anaphylactic shock. In regard to the isolation of human-derived thrombomodulins, there are some reports as described below. In the following explanation, molecular weights of the human-derived thrombomodulins, if not otherwise stated, are the results of measurements by sodium dodecyl sulfate polyacrylamide gel electrophoresis (SDS-PAGE) under non-reduced condition.

P. W. Majerus et al. purified thrombomodulin from human placenta and reported its molecular weight as 75,000 [J. Biol Chem., Vol 259, p.12246 (1984)]. I. Maruyama et al. isolated thrombomodulin from human lung, which has activities similar to those of thrombomodulin from human placenta [J. Clin. Invest., Vol. 75, p.987 (1985)]. N. Aoki et al. isolated thrombomodulin from human placenta and reported its molecular weight as 71,000 [Thrombosis Res., Vol. 37, p.353 (1985); and Japanese Patent Application Laid-Open Specification No. Sho 60-199819]. K. Suzuki et al. partially purified thrombomodulin from human platelets and determined its molecular weight as 78,000. They concluded in the report that all of, thrombomodulins obtained from human platelets, ones from human placenta and ones from human lung hemangio endothelial cells have similar activities by comparing their behaviors in SDS-PAGE, affinities to thrombin and substrate-affinities to protein C [J. Biochem., Vol. 104, p.628 (1988)].

There are also some reports about other substances which have activities similar to above-mentioned human thrombomodulins as described below.

P. W. Majerus et al. partially purified substances with molecular weights of 63,000 and 54,000 from human serum and also indicated that similar substances exist in human urine [J. Clin. Invest., Vol. 75, p.2178 (1985). H. Ishii et al. reported that substances with molecular weights of 105,000, 63,000, 60,000, 33,000, 31,000 and 28,000 (Whether these were measured under reduced or non-reduced condition is not clearly described) are excreted in human urine 108th. Yakugakkai abstract 6F05, 11-1 (1988)].

Further, other substances with molecular weights of 200,000, 48,000 and 40,000 from urine [Japanese Patent Application Laid-Open Specification No. Sho 63-30423], and substances with molecular weights of 39,000 and 31,000 [Japanese Patent Application Laid-Open Specification Sho No. 63-146898] from urine are reported.

Meanwhile, by means of genetic engineering techniques, K. Suzuki et al. deduced the entire 557-amino acid sequence of human thrombomodulin from human lung cDNA clones [EMBO Journal, Vol 6. p.1891 (1987)]. They produced a series of peptides, which contain repeated Epidermal Growth Factor (EGF)-like structures in human thrombomodulin, by recombinant DNA techniques, and measured the effect of each peptide on thrombin-catalyzed protein C activation. Based on the obtained result, they concluded that all of the structure from the fourth through sixth EGF-like structures, which corresponds to 345th through 462nd amino acid residues numbered from amino-terminal of human thrombomodulin, is required for the exertion of thrombomodulin-like activity [J. Biol. Chem., Vol. 264, p.10351 (1989) and 12th. International Conference on Thrombosis and Hemostasis program, p.334 (1989)].

The human thrombomodulins which have been already reported are obtained from human placenta, human lung or human platelets. They are not suitable for mass production because these materials could not be supplied in large quantities. Moreover, these thrombomodulins are difficult to handle, because some detergents are necessary in order to solubilize them. Contamination by detergents is unfavorable for clinical use of these thrombomodulins.

On the other hand, previously reported thrombomodulin-like substances have neither high activity of protein C activation nor efficient anticoagulant activity per unit protein. Accordingly, a novel thrombomodulin-like substance which is physiologically more active and more valuable in medical use is earnestly expected.

In the conventional processes for the purification of the thrombomodulin-like substances from human urine, some proteinase inhibitors such as aprotinin or bestatin are used to prevent the substances from decomposition. There are, however, other enzymes such as uropepsin which can not be completely inhibited by these proteinase inhibitors, and a complete prevention of the thrombomodulin-like substances from decomposition can not be easily achieved by these processes.

Further, since thrombomodulin is a glycoprotein, genetic engineering techniques could not provide a substance which possesses sugar chains completely equal to those of human thrombomodulin. Differences in sugar chains may cause unfavorable properties such as some side effects. For these reasons, it has been desired to obtain a thrombomodulin-like substance which resembles more closely to a native human thrombomodulin.

SUMMARY OF THE INVENTION

An object of the present invention is to provide a novel anticoagulant substance with thrombin-binding properties derived from human urine.

Another object is to provide a process for preparation of the same.

The other object is to provide a pharmaceutical composition, which comprises the said anticoagulant substance as an active component, for prevention and/or treatment of diseases related to the disorders in blood coagulation system.

The substance of the present invention has a different molecular weight and different carboxy-terminal amino acid sequence from those of previously isolated thrombomodulin-like substances. The substance has remarkably high activity of thrombin-catalyzed protein C activation and a potent anticoagulant effect, and gives superior in vivo effects.

DETAILED DESCRIPTION OF THE INVENTION

As a result of extensive investigations concerning development of anticoagulant substances in human urine, the present inventors have found a novel thrombomodulin-like substance, which has a different molecular weight as compared to previously isolated thrombomodulin-like substances, a remarkably high activity of thrombin-catalyzed protein C activation, a potent anticoagulant effects and superior physiological effects, and have finally accomplished the present invention.

According to the present invention, the anti-coagulant substances of the present invention may be prepared by purification from fresh or concentrated human urine by suitably combining ion-exchange chromatography, affinity chromatography using thrombin-bound resin, gel filtration chromatography, adsorption chromatography, hydrophobic chromatography and/or polyacrylamide gel electrophoresis after alkalization and heat-treatment.

The process for preparation of substance of the present invention is practiced, for example, in the following manner. Human urine is firstly adjusted to a pH of 8 to 9, preferably to $8.3\pm0.3$, for the purpose of inactivation of contaminating proteinases. After removal of the precipitate and neutralization of pH, the resultant solution is concentrated, for example, using an ultrafiltration membrane with a cutoff molecular weight of 10,000 to 40,000. After the pH of the concentrate is adjusted to 5 to 10, preferably to $7.3\pm0.2$, the concentrate is heat-treated at a temperature of 50° to 70° C. for 5 to 45 min., preferably at $60°\pm5°$ C. for 15 5 min., in order to inactivate residual proteinases. The concentrate is then subjected to anion-exchange chromatography which had been equilibrated at pH 5.5 to 7.5, more preferably at pH $6.5\pm0.2$ to adsorb active components. The active components is then eluted with a buffer at pH of 2 to 4.5, preferably at pH $4.0\pm0.05$. The eluate containing the active components is desalted and concentrated, for example, using an ultrafiltration membrane with a cutoff molecular weight of 10,000 to 40,000 and is adsorbed to an affinity column, where thrombin is used as a ligand. The column is then washed with a buffer containing 0.05 to 0.8M, preferably 0.1 to 0.7M, of NaCl, and is eluted with a buffer containing 0.9 to 2.0M, more preferably $1.0\pm0.05$M, of NaCl. The collected fractions are concentrated and, if necessary, the thrombin affinity chromatography is repeated. If it is necessary, the eluted active fraction is passed through a gel-filtration column repeatedly, and active fractions corresponding to the substance of the present invention (TM1 or TM2, which will be described thereafter) are collected. Alternatively, the above-mentioned concentrated eluate from thrombin affinity chromatography can be subjected to SDS-PAGE to obtain the substance of present invention. The substance may be heat-treated at 60° C.$\pm2°$ C. for 10 hrs. in order to inactivate contaminating viruses to be in a more suitable form as a pharmaceutical composition.

Diethyl amino ethyl-(DEAE-) Cellulose, DEAE-Sepharose, DEAE-Cellulofine, DEAE-Toyopearl or the like can be used as anion-exchange resins in above-mentioned purification process. A thrombin affinity column can be obtained by binding thrombin to resins such as cellulose, agarose or dextran by using cyanogen bromide, followed by a treatment with diisopropyl-fluorophosphate, phenylmethansulfonyl fluoride or the like. As resins for gel filtration, Sephacryl S-200, Sephacryl S-300, Sephadex G-100, G-150, G-200, Toyopearl HW-55, Biogel P-100, P-150, Sepharose 6B or the like can be used.

According to above-mentioned procedure, the anticoagulant substance of the present invention can be obtained as a purified form. Other substances (TM3 or TM4, which will be described hereafter) having characteristics similar to the substance of the present invention can be obtained by utilizing the method described above.

The anticoagulant substances of the present invention and related substances are characterized by following properties;

(a) Molecular weight
  TM1: $72,000\pm3,000$
  TM2: $79,000\pm3,000$
  TM3: $94,000\pm3,000$
  TM4: $114,000\pm3,000$ Method of the determination:

Molecular weight was determined by SDS-PAGE according to the method of Laemmli [Nature vol 227, p.680, (1970)] using 7.5% polyacrylamide gel. under non-reduced condition. "Molecular weight standard kit" (product of Seikagaku Kogyo Co., Japan) and phosphorylase A (product of Boeringer Mannheim Yamanouchi, West Germany) were used as standard proteins. Electrophoresis was carried out at a constant current of 7 mA for 20 hrs. As shown in the result, the molecular weight of TM1 is obviously different from that of TM2.

(b) Amino acid composition (mol %):

| Aspartic acid | 9.5 ± 2.0 | Methionine | 1.1 ± 0.5 |
|---|---|---|---|
| Threonine | 4.0 ± 1.5 | Isoleucine | 2.8 ± 1.5 |
| Serine | 5.1 ± 1.5 | Leucine | 7.5 ± 2.0 |
| Glutamic acid | 10.9 ± 2.5 | Tyrosine | 1.6 ± 1.5 |
| Proline | 9.3 ± 1.5 | Phenylalanine | 3.7 ± 1.5 |
| Glycine | 11.0 ± 3.0 | Histidine | 2.5 ± 1.0 |
| Alanine | 11.7 ± 3.0 | Lysine | 0.8 ± 0.5 |
| Cysteine | 8.0 ± 4.0 | Arginine | 4.6 ± 1.5 |
| Valine | 5.9 ± 1.5 | | |

Method of the Determination

After 1 mg of the substance of present invention was completely acid-hydrolyzed according to the method of Moore et al. [Methods in enzymol., vol.6, p.819, (1963)], amino. Amino acid composition was analyzed by amino acid analyzer (product of Beckman Co., West Germany).

Amino acid compositions of TM1 and TM2 are the same.

(c) Terminal amino acid sequence

Amino terminal: Ala—Pro—Ala—Glu—Pro—Gln—Pro—Gly—
Gly—Ser—Gln—Cys—Val—Glu—His—Asp—
Cys—Phe—Ala—Leu—Tyr—Pro—Gly—Pro
Ala—Thr—Phe—Leu—

Carboxy terminal: —Leu—Ala—Arg (Wherein Ala represents an alanine residue, Pro a proline residue, Glu a glutamic acid residue, Gln a glutamine residue, Gly a glycine residue, Ser a serine residue, Cys a cysteine residue, Val a valine residue, His a histidine residue, Asp an aspartic acid residue, Phe a phenylalanine residue, Leu a leucine residue, Tyr a tyrosine residue, Thr a threonine residue and Arg an arginine residue.)

Method of the Determination

Twenty-five mg of the substance of the present invention was reduced and carboxymethylated according to the method of C. H. Hirs [Methods in Enzymol., vol.11, p.199, (1967)]and subjected to terminal amino acid sequence analysis. Amino terminal sequence was determined using a gas phase amino acid sequencer (product of Applied Biosystems Co., Type 470A, USA). Carboxy terminal sequence was determined by digestion with carboxypeptidase P (product of Peptide Institute Inc., Japan) according to the method of S. Yokoyama [Biochem. Biophys. Acta., vol. 397, p.443, (1975)], followed by amino acids analysis using an amino acids analysis system (product of Nihonbunko Co., Japan).

Terminal amino acid sequences of TM1 and TM2 are the same.

As shown in the result, the amino terminal amino acid sequence of the substance of the present invention is completely consistent with the results already reported. However, the carboxy terminal amino acid sequence of the substance of the present invention, -Leu-Ala-Arg, is in good agreement with the amino acid sequence in 454th through 456th position of the molecule in Suzuki's report. Namely, the carboxyl terminal of the substance of the present invention is in the position 6 amino acid residues shorter than the carboxy terminal of a peptide having amino acid sequence in 345th through 462th position of the molecule in Suzuki's report, which they insist to be a minimal active unit for the cofactor activity on thrombin-catalyzed protein C activation. This indicates that the complete amino acid sequence of the minimal active unit in Suzuki's report is not necessary for exertion of the activity. The substance provided by the present invention includes an isomer, in which the second amino acid from the carboxy terminal indicated above, alanine, is replaced with valine, because similar substitution in corresponding position of human thrombomodulin is already well known.

| (d) Sugar composition (W/W %) | |
|---|---|
| TM1: | |
| Neutral sugar: | 5.5 ± 1.0 |
| Amino sugar: | 2.2 ± 1.0 |
| Sialic acid: | 2.8 ± 1.5 |
| TM2: | |
| Neutral sugar: | 6.2 ± 1.0 |
| Amino sugar: | 3.1 ± 1.0 |
| Sialic acid: | 3.8 ± 1.5 |

Method of the Determination

Neutral sugar was determined by phenol-sulphuric acid method [Nature vol.168, p.107, (1951)]. Amino sugar was determined according to the method of Elson-Morgan (Blix's modification) [Acta. Chem. Scand., vol.2, p.467, (1948)] after the substance of present invention was heat-treated at 100° C. for 4 hrs in 4N HCl solution. Sialic acid was determined by the method of Warren [J. Biol. Chem.. vol.234. p.1971. (1959)] after the substance of present invention was heat-treated at 80° C. for an hour in 0.1N HCl solution.

The sugar composition of TM1 and TM2 are a little different from each other.

(e) Absorbance at 280 nm (in 1% aqueous solution, 1 cm light path)
TM1: 7.7±1.0
TM2: 6.7±1.0

Method of the Determination

Ten mg of freeze-dried substance of the present invention was dissolved in 1 mL of distilled water and suitably diluted. Absorbance at 280 nm was measured by spectrophotometer (Hitachi Co. type 3200, Japan) with 1 cm light path and $E^1$% (280 nm) was calculated.

(f) Isoelectric point
TM1: 3.9±0.2
TM2: 0.8±0.2
TM3: 3.8±0.2
TM4: 3.7±0.2

Method of the Determination

Isoelectric point was measured by isoelectric electrophoresis using Ampholite (product of LKB Co., pH 2.5 to 4.5, Sweden). Electrophoresis was carried out at a voltage of 500V for 40 hrs.

(g) Stability

The results of stability tests were summarized in Table 1;

TABLE 1

| Conditions | Residual activity(%) | |
|---|---|---|
| | TM1 | TM2 |
| 1. 1% mercaptoethanol(V/V) | 0 | 0 |
| 2. 1% SDS(W/V) | 80 | 82 |
| 3. 8 M urea | 93 | 92 |
| 4. 6 M guanidine-HCl | 100 | 100 |
| 5. pH 2.0 | 100 | 100 |
| 6. pH 10.0 | 91 | 93 |
| 7. 60° C. for 300 min | 95 | 94 |

As for conditions No.1 through 6, 60 μg/mL of the substance of the present invention was treated under indicated conditions at a temperature of 25° C. for 150 min. As for condition No.7, 60 μg/mL of the substance of the present invention was treated at pH of 7.5. Resultant samples were diluted 100 fold and subjected to measurement of thrombin catalyzed protein C activating cofactor activity. Assay method of protein C activation was described thereafter. Residual activity was expressed as percentages compared with nontreated sample. The substance of the present invention is stable in 1% SDS, 8M urea or 6M guanidine-HCl but is readily inactivated by reduction with mercaptoethanol. It is stable even in low or high (2 or 10) pH conditions, and is also stable after heating at 60° C. for 300 min.

(h) Solubility

The substance of the present invention (TM1 and TM2) can be dissolved in distilled water at a concentration of 30 mg protein/ml or more at room temperature.

As described above, the substance of the present invention is a novel substance which has a molecular weight different from those of previously reported thrombomodulins. The substance is more advantageous than thrombomodulins extracted from placenta or lung, previously because detergents are not necessary for its solubilization.

The substance of the present invention has following effects.

(1) Affinity to thrombin (anti-thrombin activity)

(a) The substance of the present invention was adsorbed almost 100% by DIP-thrombin-agarose gel-chromatography.

(b) One hundred μL of a solution containing TM1 and 100 μL of bovine thrombin (1 U/mL, product of Mochida Pharmaceutical Co., Japan) were mixed and incubated at 37° C. for 30 min. One hundred μL of Human fibrinogen solution (2 mg/mL) was then added to the mixture to measure clotting time using coagulometer (product of Amerung Co., West Germany). Results are shown in Table 2.

TABLE 2

| Drugs | Conc.(OD280) | Clotting time(sec) |
|---|---|---|
| Control | — | 41.2 |
| TM1 | 0.01 | >900 |
| TM2 | 0.01 | >900 |

As shown in Table 2, the substance of the present invention possesses an ability to bind thrombin and inhibit its coagulant activity.

The results shown in Table 2 indicate that the anti-thrombin activities of the substances are more than 50 to 60 times as potent as that of human thrombomodulin which was previously reported. This can be assured, for example, by following comparison. The effect of thrombomodulin purified from human placenta on clotting time, which was cited in Japanese Patent Application Laid-Open Specification No. Sho 62-169728, is shown as a reference in Table 3. According to the specification, the human placental thrombomodulin was proved to be more than twice as potent as previously reported human thrombomodulins. It can be concluded that the anticoagulant activity of the substance of the present invention is more potent that of previously reported thrombomodulins by comparing Table 2 with Table 3.

TABLE 3

| Drugs | Conc.(OD280) | Clotting time(sec) |
|---|---|---|
| Control | — | 35.8 |
| human placental thrombomodulin | 0.42 | 62.3 |
| | 0.84 | 109.9 |

The anticoagulant effect of human urine-derived thrombomodulin, which was cited in Japanese Patent Application Laid-Open Specification No. Sho 63-30423, is shown as a reference in Table 4. By comparing Table 2 with Table 4, it becomes also clear that the substance of the present invention possesses anticoagulant activity that is much more potent than previously reported human thrombomodulins.

TABLE 4

| Drug | Conc.(OD280) | clotting time(sec) |
|---|---|---|
| Control | — | 53.4 |
| human urinary thrombomodulin | 0.1 | >500 |

(2) Stimulatory effect on thrombin-catalyzed activation of protein C

Stimulatory effect of TM1 and TM2 on thrombin-catalyzed activation of protein C was examined using rabbit thrombomodulin (product of American Diagnostica Inc., USA ) as a standard. Namely, 20 μL of bovine thrombin solution (10 U/mL, product of Mochida pharmaceutical Co., Japan) mixed with 60 μL of 0.1M Tris HCl buffer (pH 7.5) and 10 μL of various concentration (0 to 15 μg/mL) of either rabbit thrombomodulin, TM1 or TM2. Ten μL of human protein C (product of American diagnostica Inc., USA) solution (500 μg/mL) was added to the mixture. After 30 min pf reaction at 37° C., reaction was stopped by an addition of 150 μL of equivolume mixture of 1 U/mL human antithrombin III (product of Green Cross Co., Japan) solution and 10 U/mL heparin (product of Mochida Pharmaceutical Co. Japan) after 15 min. of incubation at 37° C., 250 μL of a synthetic substrate (Tert-butoxycarbony-Leu-Ser-Thr-Arg-MCA, product of peptide Institute Inc., Japan) solution (0.1 mM) was added to the reaction mixture, and then incubated at 37° C. for 10 min. Five hundred μL of 20% acetic acid solution was added to the mixture for the termination of the reaction, followed by a measurement of fluorescence of the released 7-amino-4-methyl-coumarin (AMC) using a fluorospectrophotometer at an excitation wave length of 380 nm and emission at 460 nm. The amount of TM1 or TM2 which is equivalent to 1 mg of rabbit thrombomodulin in activating thrombin-catalyzed protein C was calculated using a calibration curve obtained as described above, and was expressed as 1 mg equivalent to rabbit thrombomodulin (mg eq.).

As a result, the specific activities of TM1 and TM2 are 2.3 and 2.2 mg eq./mg protein [protein was determined according to the method of Lowry et al. J. Biol. Chem., Vol.156, p.564 (1945)], respectively. This result indicates that the substance of the present invention possesses evident abilities of protein C activation in combination with thrombin, and that the abilities of the substances of the present invention are more potent than that of previously reported thrombomodulins.

(3) Anticoagulant activity

One hundred μL of citrated human platelet poor plasma (PPP) and 10 μL of the substance of the present invention in various concentrations (10 to 1000 μg eq./mL) was mixed and incubated at 37° C. for 2 min. One hundred μL of thrombin (2 U/mL, Green Cross Co., Japan) was added to the mixture for the measurement of clotting time. Average of three experiments is shown in Table 5.

TABLE 5

| Drugs | Amount(μg eq.) | Clotting time(sec) |
| --- | --- | --- |
| Control | — | 22.7 |
| TM1 | 0.1 | 23.8 |
|  | 1 | 31.2 |
|  | 10 | 188.8 |
| TM2 | 0.1 | 22.9 |
|  | 1 | 32.0 |
|  | 10 | 195.5 |

As shown in the results, the substance of the present invention prolongs the clotting time significantly.

In vivo anticoagulant effect of the substance of the present invention is explained using experimental examples provided hereafter.

Experimental example 1

Figure 1:
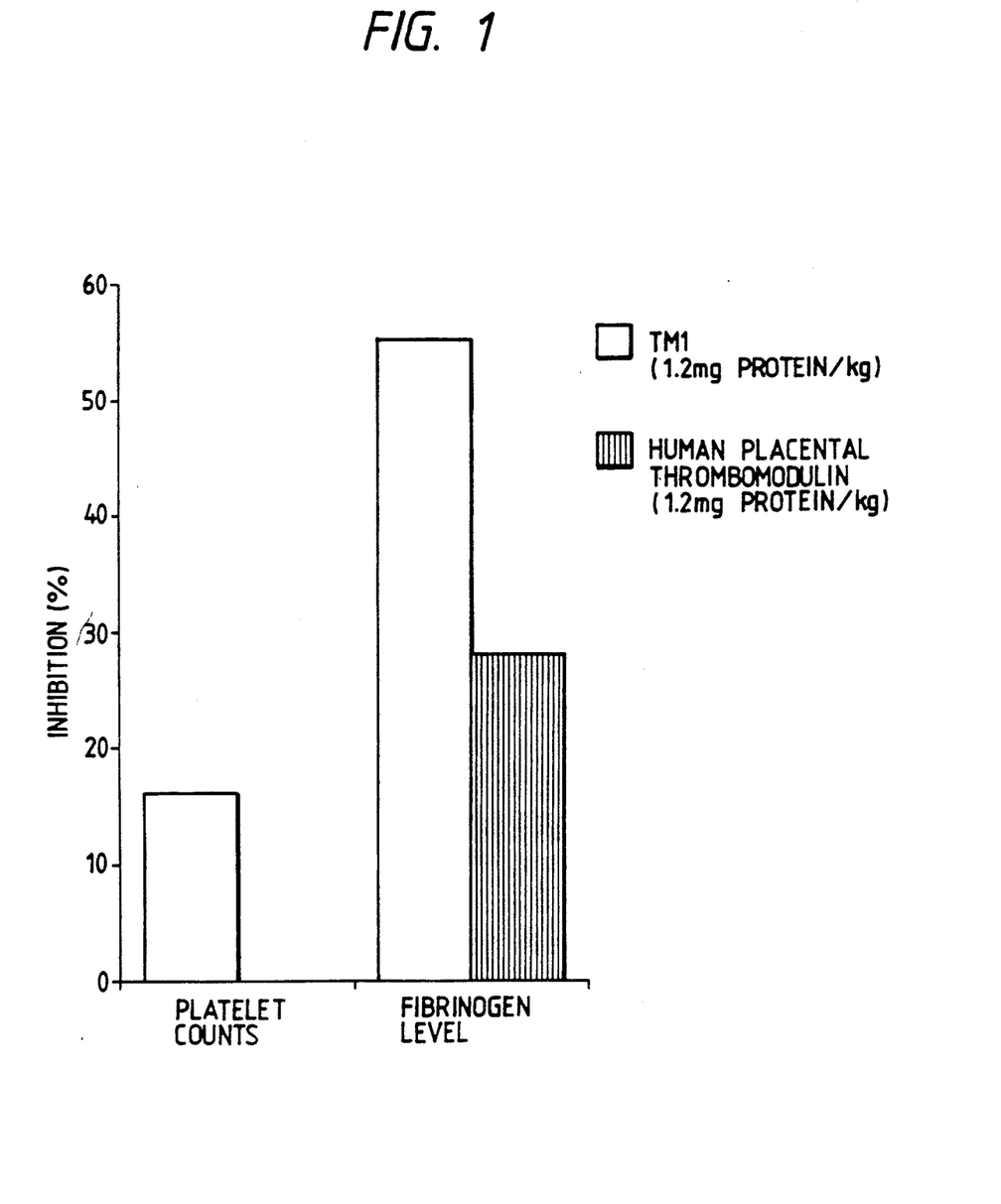
FIG. 1 illustrates the effects of TM1 and human placental thrombomodulin on endotoxin induced disseminated intravascular coagulation (DIC) model in rats.

Effect on endotoxin-induced disseminated intravascular coagulation (DIC) model in rats The experiment was performed according to the method of T. Yoshikawa et al. [Nippon Ketsuekigakkai Zasshi, vol.45 (3), p.633–640, (1982)]. Female Wistar rats weighing 160–200 g were anesthetized with pentobarbital, and lipopolysaccharide (product of Difco Laboratories, USA) was infused at a dose of 25 mg/kg in 4 hrs to establish DIC model. Either TM1 or human placental thrombomodulin dissolved in 0.01M phosphate buffer (pH 7.0) containing 0.1% human serum albumin and 0.14M NaCl was infused simultaneously for 4 hrs. at a dose of 1.2 mg protein/kg. Lubrol (0.005%) was added to the solution in case of human placental thrombomodulin for the purpose of solublization. Blood samples were taken before and after the drug infusion and platelet count and plasma fibrinogen level were measured. In control group, only the vehicle was infused instead of drug solution. The result is expressed as percent inhibition as compared to the control as shown in FIG. 1. Inhibition was calculated as follows.

Inhibition (%):
[(Decrease in the control group) −

(Decrease in the administered group)]/

(Decrease in the control group) × 100.

Decreased platelet count and plasma fibrinogen level in rat endotoxin DIC model were significantly restored by the injection of TM1.

EXPERIMENTAL EXAMPLE 2

Effect on thromboplastin-induced DIC model in rats

Figure 2:
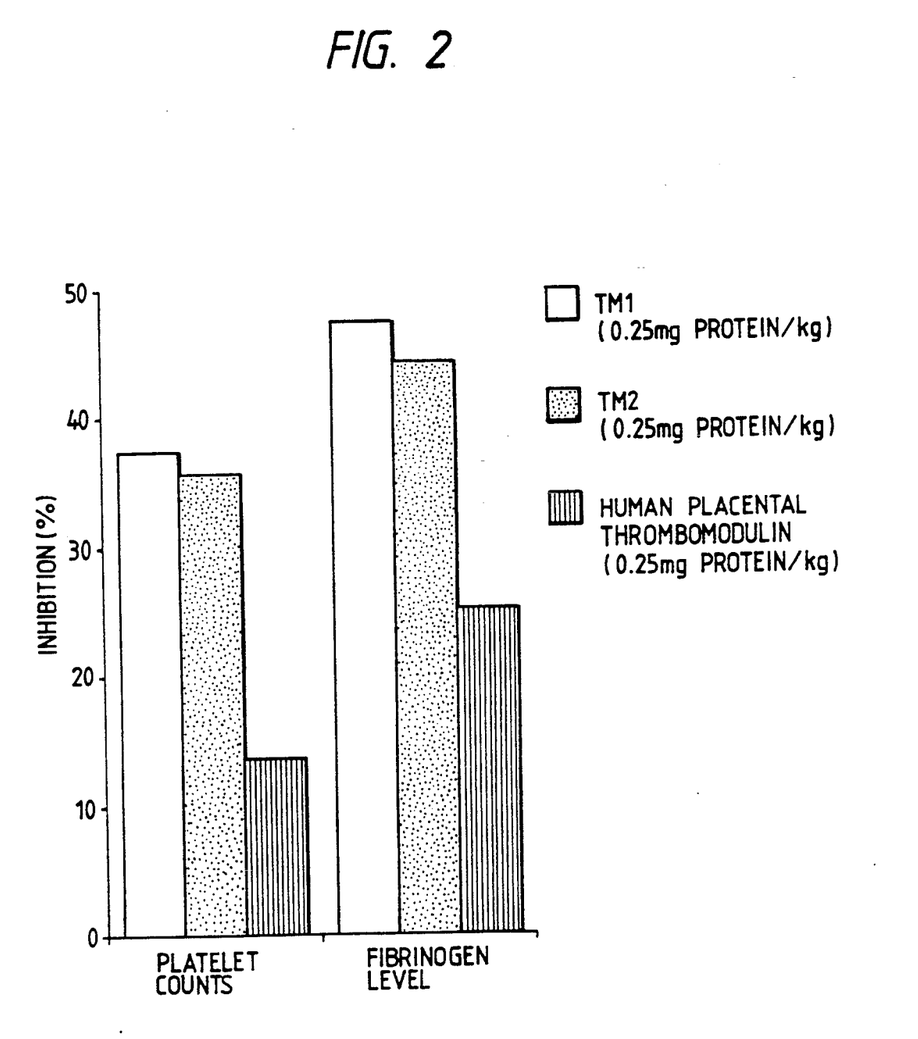
FIG. 2 illustrates the effects of TM1, TM2 and human placental thrombomodulin on thromboplastin induced DIC in rats.

The experiment was performed according to the method of H. Ohno et al. [Thrombosis Res., vol.24, p.445, (1981)]. Male Wistar rats weighing 240–270 g were anesthetized with ethyl carbamate and thromboplastin (Simplastin ®, product of Organon Teknika Corp., USA) was infused at a dose of 25 mg/kg in 20 min. to establish DIC model. Either TM1, TM2 or human placental thrombomodulin dissolved in 0.01M phosphate buffer (pH 7.0) containing 0.1% human serum albumin, 0.14M NaCl and 0.01% Lubrol was infused at a dose of 0.25 mg protein/kg for 90 min. starting 30 min. before the beginning of the thromboplastin injection. Blood samples were taken before and after the drug infusion and platelet count and plasma fibrinogen level were measured. In the control group, only the vehicle was infused instead of drug solution. The result is expressed as percent inhibition as compared to the control as shown in FIG. 2. Inhibition was calculated in the same manner as in Experimental example 1.

Decreased platelet count and plasma fibrinogen level in this DIC model were also significantly restored by the injection of TM1 or TM2.

The in vivo effect of TM1 or TM2, as well as in vitro effect, was proved to be more potent than that of previously reported thrombomodulins. In another aspect, since the thrombomodulin-like substance synthesized by Suzuki et al utilizing genetic engineering techniques possesses anticoagulant activity equal to the existing thrombomodulins purified from human tissues [EMBO J. vol.6, p.1891, (1987) and Japanese Patent Application Laid-Open Specification No. Hei 1-6219, (1989)], it is clear that the effects of the substance of the present invention is more potent than that of recombinant thrombomodulin-like substances.

EXPERIMENTAL EXAMPLE 3

Acute toxicity test in mice

Acute toxicities of the substance of the present invention was examined. Ten male ddY mice were intravenously injected TM1 or TM2 at a dose of 200 mg eq./kg. Neither serious side effects nor death was observed in 7 days after the drug administration.

As described above, the substance of the present invention possesses a potent anticoagulant effect in vivo as well as in vitro, and the potency of these effects were higher than those of existing thrombomodulins. The safety of the substance of the present invention was also demonstrated.

The substance of the present invention may be used, for example, for the treatment and prevention of diseases related to disorders in blood coagulation systems, such as DIC, various types of thrombosis, obstruction of peripheral blood vessels, myocardial infarction, brain infarction, transient ischemic attack, gestosis and liver or kidney insufficiency.

The present substance may be employed as pharmaceutical compositions such as injections, inhalants and suppositories, preferably injections, containing the present substances with appropriate, pharmaceutically acceptable carriers or medium such as sterilized water, physiological saline, edible oils, non-toxic organic solvents or non-toxic solubilizer such as glycerin or propylene glycol. The composition may be mixed with auxiliary agents which is conventional in pharmaceutical art such as excipients, binders, coloring agents, corrigents, emulsifying agents, suspending agents, stabilizing agents or preservatives.

When the compositions are injections, they may be administered once or divided 2 to 6 times or by instillation, etc. While dose varies depending upon age, body weight and condition of the patient, conditions and kinds of diseases, etc., from 0.05 to 500 mg eq., preferably from 0.1 to 10 mg eq., can be used as a daily dose for an adult.

In addition, the substance of the present invention may be used for the prevention of blood coagulation by being bound to the surface of medical implements such as artificial blood vessels, artificial organs or catheters using bridging agents or the like.

EXAMPLES

The process for the preparation of the substance of the present invention will be described in more detail with reference to the following Examples, which are not intended to be limiting the scope of the present invention unless otherwise specified.

EXAMPLE 1

Figure 3:
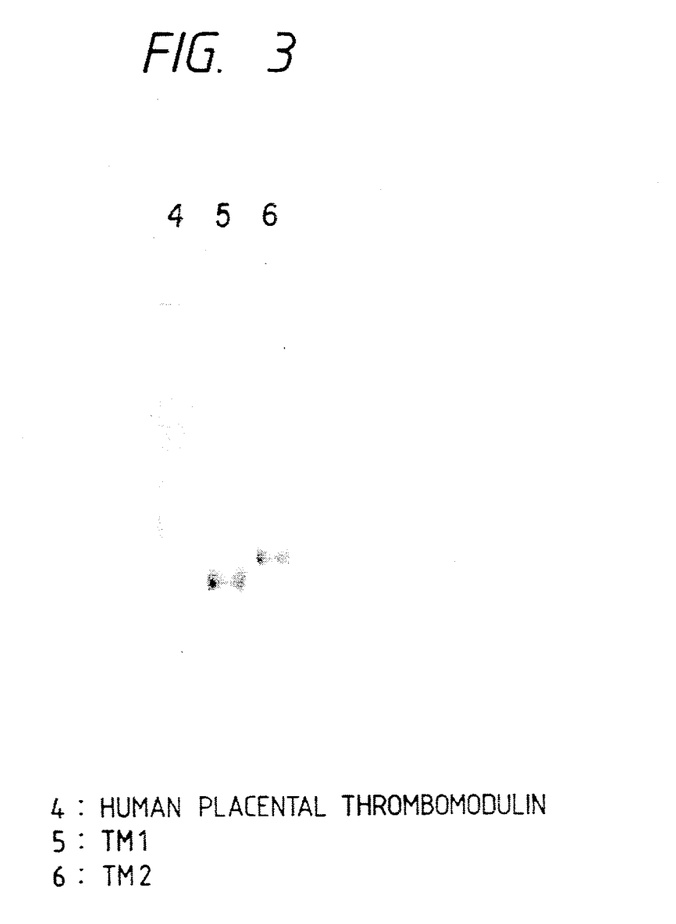
FIG. 3 illustrates SDS-PAGE of TM1, TM2 and human placental thrombomodulin under non-reduced conditions.

One hundred L of fresh human urine obtained from healthy males with the use of preservatives, for example phenol, was adjusted to pH 8.5 using 10% NaOH solution, and the precipitate was removed. After being adjusted to pH 5.5 using 4M HCl, the urine was filtrated by acrylonitril fibers for the purpose of adsorption of urokinase, and concentrated using an ultrafiltration membrane filter with a cutoff molecular weight of 40,000. The concentrate is adjusted to pH 7.3, and heat-treated at a temperature of 60 ° C. for 15 min. The concentrate was then subjected to DEAE-cellulose (product of Whatman Co., USA) column (300 mL) which had been equilibrated with a 0.05M phosphate buffer (pH 6.5) containing 0.068M NaCl to adsorb an active component, followed by washing with 750 mL of the same buffer as used in the equilibration and then eluted with an acetate buffer (pH 4.0) containing 0.05M NaCl. After desaltation and concentration of the active eluent by ultrafiltration membrane with a cutoff molecular weight of 30,000, the pH of the concentrate was adjusted to 7.5 using 2M NaOH. The concentrate was then passed through a DIP-thrombin-agarose column (2.5 mL) which had been equilibrated with a 0.02M Tris HCl buffer (pH 7.5) containing 0.1M NaCl, 1 mM benzamidine HCl and 0.5 mM $CaCl_2$ to adsorb active components. The column was washed with 25 mL of the same buffer as used in the equilibration, and was eluted with a 0.02M tris HCl buffer (pH 7.5) containing 1.0M NaCl, 1 mM benzamidine HCl and 0.5 mM EDTA. The active fraction is then dialysed against the same buffer as used in the equilibration and adsorbed again to the DIP-thrombin-agarose column which had been equilibrated in the same condition as described above. The columnwas washed with 10 mL of the same buffer as used in the equilibration, and washed again with 10 mL of 0.02 mM Tris HCl buffer (pH 7.5) containing 0.8M NaCl, 1 mM benzamidine HCl and 0.5 mM $CaCl_2$. The active fraction was then eluted with 0.02 mM Tris HCl buffer (pH 7.5) containing 1.0M of NaCl, 1 mM benzamidine HCl and 0.5 mM EDTA. After being concentrated using an ultrafiltration membrane with a cutoff molecular weight of 30,000, the eluted active fraction was passed, through, a Sephacryl S-300 (product of Pharmacia Fine Chemical Co.) column (500 mL) which had been equilibrated with 0.01M phosphate buffer (pH 7.0) containing 0.14M NaCl and then the active fraction was collected. The fraction was again subjected to the Sephacryl S-300 column in the same condition as before, to obtain the substance of the present invention. The amount of purified TM1 and TM2 are 247 and 166 µg eq., respectively. SDS-PAGE patterns of the purified substances and human placental thrombomodulin described in Reference Example were shown in FIG. 3. The molecular weights of TM1 or TM2 were disinctly different from that of human placental thrombomodulin. Each of the substances was demonstrated as a single band on the SDS-PAGE.

Typical examples of formulations of the present invention will be shown below.

| Example 2: freeze-dried parenteral injection | |
|---|---|
| TM1 | 20 mg eq. |
| Purified gelatin | 50 mg |
| Sodium phosphate | 34.8 mg |
| Sodium chloride | 81.8 mg |
| Mannitol | 25 mg |

The above components were dissolved in 10 mL of distilled water for injection. The obtained solution was sterilized by filtration, and 1.0 mL each of this solution was put into sterilized vials, freeze-dried and sealed by ordinary methods, to produce a freeze-dried preparation for parenteral injections.

| Example 3: freeze-dried parenteral injection | |
|---|---|
| TM2 | 40 mg eq. |
| Albumin | 20 mg |
| Sodium phosphate | 34.8 mg |
| Sodium chloride | 81.8 mg |
| Mannit | 25 mg |

The above components were dissolved in 10 mL of distilled water for injection. The obtained solution was sterilized by filtration, and 1.0 mL each of this solution was put into sterilized vials, freeze-dried and sealed by ordinary methods, to produce a freeze-dried preparation for parenteral injections.

REFERENCE EXAMPLE

An example of the preparation of human placental thrombomodulin

Human placental thrombomodulin was purified according to the method of N. Aoki et al [Japanese Patent Application Laid-Open Specification No. Sho 60-199819]. Shortly, thirty human placentae (about 12 kg) were washed with 0.02M tris-HCl buffer (pH 7.5) containing 0.25M sucrose and 1 mM benzamidine HCl and ground into a homogenous liquid mixture. The homogenized mixture was centrifuged at 3,000 rpm for 40 min. to collect a precipitate. The precipitate was suspended in the buffer mentioned above, stirred for 10 min and again centrifuged to collect a precipitate. The above procedure was repeated for three times using 20 L of the buffer each time and the precipitates obtained were combined together and extracted with 60 L of 0.02M tris-HCl buffer (pH 7.5) containing 0.25M sucrose, 1 mM benzamidine HCl and 0.5% (V/V) Triton X-100 (product of Sigma) to obtain a crude extract. The protein content of the crude extract was 46.7 g (Protein was determined according to the method of Lowry et al. The method hereawfter was the same unless otherwise specified.). The crude extract (60 L) was applied to a DIP-thrombin-agarose column (4φ×16 cm) which had been equiliberated with 0.02M Tris HCl buffer (pH 7.5) containing 0.1M NaCl, 0.5mM $CaCl_2$, 0.1 mM benzamidine HCl and 0.5% (V/V)Triton X-100. The column was then washed with 2 L of the same buffer as used in the equilibration. The column was then eluted using a 0.02M tris-HCl buffer (pH 7.5) containing 1 mM NaCl, 0.1 mM EDTA, 1 mM benzamidine HCl and 0.5%(V/V) Triton X-100 and active fractions were collected. The volume of the eluate was 650 mL and the total protein content of the eluate was 1.7 g. The eluate was then concentrated using an ultrafiltration apparatus (Milipore Ltd.) with a cutoff molecular weight of 30,000 and applied to the DIP-thrombin-agarose column which had been treated in the same manner described above. Thereafter, the column was washed with 150 mL of a 0.02M tris-HCl buffer (pH 7.5) containing 0.4M NaCl, 0.5 mM CaCl$_2$, 0.1 mM benzamidine HCl and 0.5%(V/V) Triton X-100 and eluted by a gradient elution technique using a solution obtained by adding NaCl (0.4 to 1M to a 0.02M tris-HCl buffer (pH 7.5) containing 0.1 mM EDTA, 1 mM benzamidine HCl and 0.5%(V/V) Triton X-100. The eluate was collected in 30 mL-fractions. The net volume of the active fractions was 1,290 ml and the protein content 68 mg. The collected fraction was concentrated using ultrafiltration apparatus (Milipore Ltd.) with a cutoff molecular weight of 30,000 and passed through a S-300 (product of Farmacia Co.) column (2.6$\phi \times$90 cm) which had been equilibrated with 0.01M phosphate buffer (pH 7.0) containing 0.05% Triton X-100 and 0.14M NaCl, and the active component was collected. The obtained human placental thrombomodulin was 3.1 mg.

What is claimed is:

1. A substantially purified glycoprotein having anticoagulant activity and obtained from human urine, which is characterized by having affinity to thrombin, ability to stimulate thrombin-catalyzed protein C activation, and an amino acid composition (mol %) of

| Aspartic acid | 9.5 ± 2.0, |
|---|---|
| Threonine | 4.0 ± 1.5, |
| Serine | 5.1 ± 1.5, |
| Glutamic acid | 10.9 ± 2.5, |
| Proline | 9.3 ± 1.5, |
| Glycine | 11.3 ± 3.0, |
| Alanine | 11.7 ± 3.0, |
| Cysteine | 8.0 ± 4.0, |
| Valine | 5.9 ± 1.5, |
| Methionine | 1.1 ± 0.5, |
| Isoleucine | 2.8 ± 1.5, |
| Leucine | 7.5 ± 2.0, |
| Tryosine | 1.6 ± 1.5, |
| Phenylaline | 3.7 ± 1.5, |
| Histidine | 2.5 ± 1.0, |
| Lysine | 0.8 ± 0.5 and |
| Arginine | 4.6 ± 1.5, | as measured after complete acid-hydrolyzation according to the method of Moore et al.;
wherein the amino terminus of the glycoprotein is as follows:

Ala—Pro—Ala—Glu—Pro—Gln—Pro—Gly—Gly—Ser—Gln—Cys—Val—Glu—His—Asp—Cys—Phe—Ala—Leu—Tyr—Pro—Gly—Pro—Ala—Thr—Phe—Leu— wherein the carboxyl terminal is
-Leu-Val-Arg or -Leu-Ala-Arg; and
having stability at pH 2 to 10,
at 60° C. for 300 min.,
in 1% (W/V) SDS,
in 6M guanidine hydrochloride, and
in 8M urea;
a molecular weight of
79,000±3,000 as measured by SDS-polyacrylamide gel electrophoresis under non-reduced conditions;
a sugar composition (% W/W) of
neutral sugar: 6.2±1.0 as measured by Phenol-Sulfuric acid method,
amino sugar: 3.1±1.0 as measured by Elson-Morgan's method (Blix's modification) and
sialic acid: 3.8±1.5 as measured by Warren's method;
an absorbance at 280 nm of
6.7±1.0 (in 1% aqueous solution, 1 cm light path);
an isoelectric point of
pH 3.8±0.2; and
is water soluble.

2. A pharmaceutical composition which comprises a pharmaceutically acceptable carrier and an anticoagulant effective amount of a substantially purified glycoprotein with anticoagulant activity obtained from human urine having the following properties:
affinity to thrombin,
ability to stimulate thrombin-catalyzed protein C activation and
an amino acid composition (mol %) of

| Aspartic acid | 9.5 ± 2.0, |
|---|---|
| Threonine | 4.0 ± 1.5, |
| Serine | 5.1 ± 1.5, |
| Glutamic acid | 10.9 ± 2.5, |
| Proline | 9.3 ± 1.5, |
| Glycine | 11.0 ± 3.0. |
| Alanine | 11.7 ± 3.0, |
| Cysteine | 8.0 ± 4.0, |
| Valine | 5.9 ± 1.5, |
| Methionine | 1.1 ± 0.5, |
| Isoleucine | 2.8 ± 1.5, |
| Leucine | 7.5 ± 2.0, |
| Tyrosine | 1.6 ± 1.5, |
| Phenylalanine | 3.7 ± 1.5, |
| Histidine | 2.5 ± 1.0, |
| Lysine | 0.8 ± 0.5 and |
| Arginine | 4.6 ± 1.5, | as measured after complete acid-hydrolyzation according to the method of Moore et al.;
wherein the amino terminus of the glycoprotein is as follows:

Ala—Pro—Ala—Glu—Pro—Gln—Pro—Gly—Gly—Ser—Gln—Cys—Val—Glu—His—Asp—Cys—Phe—Ala—Leu—Tyr—Pro—Gly—Pro—Ala—Thr—Phe—Leu—;

wherein the carboxyl terminal is
-Leu-Val-Arg or -Leu-Ala-Arg; and
having stability at pH 2 to 10,
at 60° C. for 300 min.,
in 1% (W/V) SDS,
in 6M guanidine hydrochloride, and
in 8M urea;
a molecular weight of
79,000±3,000 as measured by SDS-polyacrylamide gel electrophoresis under non-reduced conditions;
a sugar composition (% W/W) of
neutral sugar: 6.2±1.0 as measured by Phenol-Sulfuric acid method,
amino sugar: 3.1±1.0 as measured by Elson-Morgan's method (Blix's modification) and
sialic acid: 3.8±1.5 as measured by Warren's method;
an absorbance at 280 nm of 6.7±1.0 (in 1% aqueous solution, 1 cm light path);
an isoelectric point of
pH 3.8±0.2; and
is water soluble.

3. A substantially purified glycoprotein having anticoagulant activity and obtained from human urine, which is characterized by having affinity to thrombin, ability to stimulate thrombin-catalyzed protein C activation, and an amino acid composition (mol %) of

|  |  |
|---|---|
| Aspartic acid | 9.5 ± 2.0, |
| Threonine | 4.0 ± 1.5, |
| Serine | 5.1 ± 1.5, |
| Glutamic acid | 10.9 ± 2.5, |
| Proline | 9.3 ± 1.5, |
| Glycine | 11.0 ± 3.0, |
| Alanine | 11.7 ± 3.0, |
| Cysteine | 8.0 ± 4.0, |
| Valine | 5.9 ± 1.5, |
| Methionine | 1.1 ± 0.5, |
| Isoleucine | 2.8 ± 1.5, |
| Leucine | 7.5 ± 2.0, |
| Tyrosine | 1.6 ± 1.5, |
| Phenylalanine | 3.7 ± 1.5, |
| Histidine | 2.5 ± 1.0, |
| Lysine and | 0.8 ± 0.5 |
| Arginine | 4.6 ± 1.5, | as measured after complete acid-hydrolyzation according to the method of Moore et al.;

wherein the amino terminus of the glycoprotein is as follows:

Ala—Pro—Ala—Glu—Pro—Gln—Pro—Gly—Gly—Ser—Gln—
Cys—Val—Glu—His—Asp—Cys—Phe—Ala—Leu—Tyr—Pro—
Gly—Pro—Ala—Thr—Phe—Leu—;

wherein the carboxyl terminal is
-Leu-Val-Arg or -Leu-Ala-Arg; and
having stability at pH 2 to 10,
at 60° C. for 300 min.,
in 1% (W/V) SDS,
in 6M guanidine hydrochloride, and
in 8M urea;
a molecular weight of
79,000±3,000 as measured by SDS-polyacrylamide gel electrophoresis under non-reduced conditions;
a sugar composition (% W/W) of
neutral sugar: 6.2±1.0 as measured by Phenol-Sulfuric acid method,
amino sugar: 3.1±1.0 as measured by Elson-Morgan's method (Blix's modification) and
sialic acid: 3.8±1.5 as measured by Warren's method,
an absorbance at 280 nm of
6.7±1.0 (in 1% aqueous solution, 1 cm light path); and
an isoelectric point of
pH 3.8±0.2;
and solubility in distilled water of at least 30 mg/ml.

* * * * *